United States Patent [19]

Samuel et al.

[11] Patent Number: 5,110,911
[45] Date of Patent: May 5, 1992

[54] HUMAN TUMOR-ASSOCIATED THOMSEN-FRIEDENREICH ANTIGEN

[75] Inventors: John Samuel; B. Michael Longenecker, both of Edmonton, Canada

[73] Assignee: Biomira, Inc., Alberta, Canada

[21] Appl. No.: 430,357

[22] Filed: Nov. 2, 1989

[51] Int. Cl.$^5$ ............ C07K 15/02; C07K 15/14; G01N 33/48; G01N 33/543

[52] U.S. Cl. ............ 530/395; 530/350; 530/413; 530/810; 530/828; 436/15; 436/87; 436/545

[58] Field of Search ............ 530/350, 395, 810, 828, 530/413; 436/15, 87, 545

[56] References Cited

U.S. PATENT DOCUMENTS 4,818,682 4/1989 Linnane ............ 436/64

OTHER PUBLICATIONS

N. Shimoda et al., J. Biochem. 102: 657-664, 1987.
Gold and Miller, Nature 255: 85-87, 1 May 1975.
Boland et al., Proc. Natl. Acad. Sci. U.S.A. 79:2051-2055, Mar. 1982.
Springer et al., Science 224:1198-1206 (1984); T and Tn, General Carcinoma Autoantigens.
Samuel et al., Cancer Research, 50:4801-8 (1990); Analysis of Human Tumor Associated Thomsen-Friedenreich Antigen.
Itzkowitz et al., Cancer Research, 49: 197-204; (1989), Expression of Tn, Sialosyl-Tn, and T Antigens in Human Colon Cancer.

Primary Examiner—Robert A. Wax
Assistant Examiner—Stephen Walsh
Attorney, Agent, or Firm—Iver P. Cooper

[57] ABSTRACT

Human tumor associated Thomsen-Friedenreich (TF) antigen is purified from adenocarcinoma conditioned media, adenocarcinoma cell detergent extracts or plural effusion fluid by affinity chromatography using an insolubilized TF-specific monoclonal antibody, MAb 49H.8. The TF antigen is a glycoprotein characterized by a non-cryptic Gal $\beta(1\to3)$ GalNAc epitope, a molecular weight in excess of 1,000,000 daltons, and extractability with perchloric acid, the epitope being sensitive to alkali and periodate but resistant to acid. A heterologous sandwich immunoassay has been developed for human TF antigen using a monoclonal antibody as the catcher and labelled peanut agglutinin as the probe. Since human TF antigen is shed by tumor cells, a positive determination of the TF antigen in a patient sample indicates the presence of cancer. The test can also be used to monitor the course of conventional chemotherapy or radiotherapy by monitoring the amount of TF antigen in a fluid sample from a patient being so treated. Because of the sensitivity of the assay method, cancer can be detected in very early stages by the assay method of the present invention.

6 Claims, 7 Drawing Sheets

FIG. I.

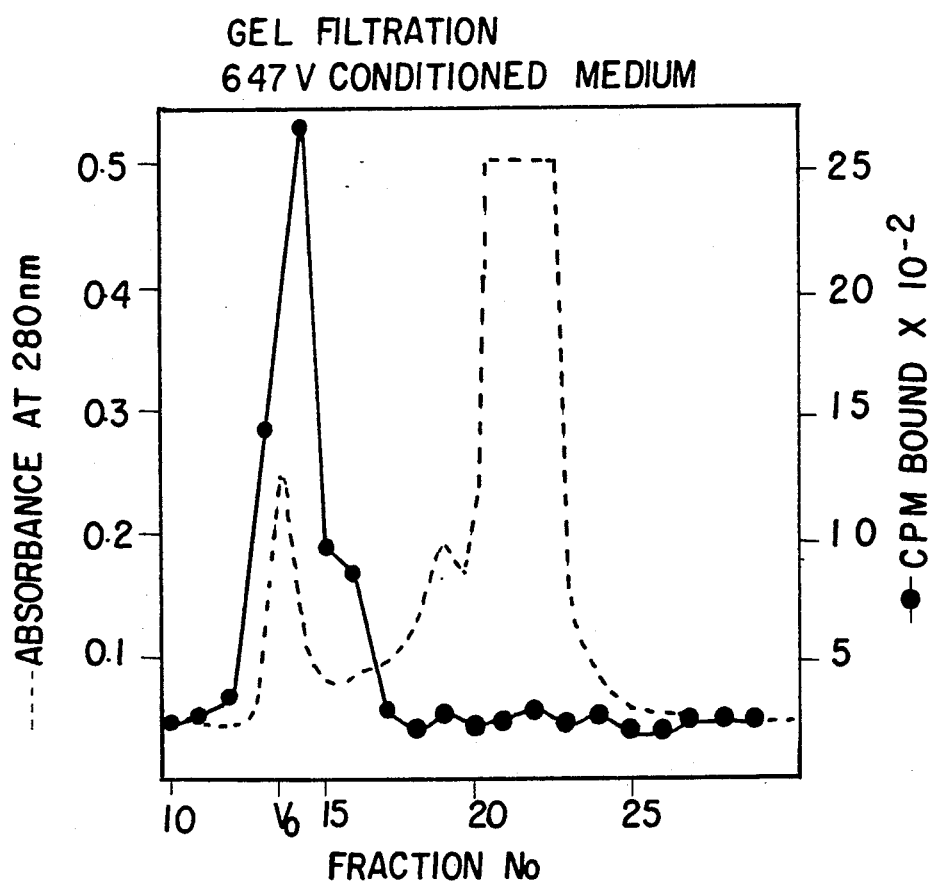

- 200

- 116.2
- 92.5

- 66.2

- 45

HUMAN TUMOR-ASSOCIATED THOMSEN-FRIEDENREICH ANTIGEN

BACKGROUND OF THE INVENTION

1. Field of the Invention

The present invention relates to a method for detecting the presence of tumor cells in the body by detecting the presence of human Thomsen-Friedenreich antigen.

2. Information Disclosure Statement

The immunodominant group of the Thomsen-Friedenreich (TF) erythrocyte antigen is characterized as [D-$\beta$-Gal (1-3)-$\alpha$-GalNAc]. The TF hapten is expressed in cryptic form in normal human red blood cells where it is a precursor structure of the M and N blood group antigens, and in normal epithelial cells. The TF hapten is revealed by removal of the terminal sialic acid residues by neuraminidase treatment.

Springer and coworkers have reported that about 90% of the human carcinomas express TF hapten in non-cryptic form [2]. The TF antigen is capable of eliciting both humoral and cell-mediated immunity in mice [3-6] and in cancer patients [7-8], and in animal models it can stimulate effective anti-cancer immunity In breast cancer patients increased expression of the TF antigen has been correlated with tumor progression and metastatic spread [9]. Studies on the expression of this antigen in bladder carcinomas suggest that it may serve as a prognostic marker [10-13]. Immunohistochemical studies on normal, premalignant, and malignant colonic tissues have shown that the expression of TF antigen is associated with malignant and premalignant changes in colonic mucosa [14-16]. Further, TF antigen has also been implicated in organotropic metastasis of tumor cells [17]. For these reasons, an assay for tumor-associated TF antigens would be of value to the clinician.

The cryptic TF antigen in red blood cells is known to be glycophorin, and has been well characterized. A murine cancer-associated TF antigen, epiglycanin, has also been subject to detailed chemical and biochemical investigations [25,26]. However, the molecular characteristics of the TF antigen expressed by human tumor cells has not yet been described.

Lectins as Diagnostic Reagents for Detecting the TF Epitope

Lectins are proteins, found mainly in plants, with the ability to specifically bind sugars, to agglutinate cells by virtue of their interaction with carbohydrate structures on cell surfaces, and to stimulate a large proportion of the lymphocytes of the immune system. For general reviews of lectins, see Lis and Sharon, "Lectins: Their Chemistry and Application to Immunology", in *The Antigens*, Vol. IV, chap. 7, pp. 429-529 (Sela, ed.; Academic Press, N.Y.; 1977); Sharon and Lis, "Lectins: Cell- Agglutinating and Sugar-Specific Proteins", Science, 177: 949-959 (1972); Lis and Sharon, "Lectins in Higher Plants", in *The Biochemistry of Plants*, Vol. 6, Chap. 10, pp. 371-447 (Marcus, ed.; Academic Press, N.Y., 1981); Lis and Sharon, "The Biochemistry of Plant Lectins (Phytohemagglutinins)", Ann. Rev. Biochem., 42: 541-574 (1973); Horowitz, et al., "Immunological Aspects and Lectins", in *The Glycoconjugates*, Vol. 2, Chap. 7, pp. 387-449 (Horowitz and Pigman, eds.; Academic Press, N.Y.; 1978).

Peanut agglutinin (PNA)[18] a is a lectin extracted from the peanut (*Arachis hypogaea*) which recognizes the immunodominant terminal disaccharide of the TF-antigen, $\beta$-D-Gal (1→3) D-GalNAc. See Lotan, et al., J. Biol. Chem., 250: 8518-23 (1975); Kania, et al., Immunobiol., 157: 154-68 (1980), Shysh, et al., Eur. J. Nucl. Med., 10:68-74 (1985).

Labeled PNA has been used for tumor imaging, see Noujaim, et al., Nucl. Med., 26: 1-6 (1987); Shysh, et al., Int. J. Cancer, 35: 113-119 (1985); Shysh, et al., Eur. J. Nucl. Med., 10: 68-74 (1985); Abdi, et al., Eur. J. Nucl. Med., 11: 350-54 (1986); for tumor histochemical analysis, see Orntoft, et al., Cancer Res., 45: 447-52 (1985) and Limas, et al., Cancer, 58: 1236-45 (1986); and in serum or other biological fluid assays for cancer markers, see Chem. Ab. 96:100527c, JP 81154660; Shamsuddin, WO88/00702; Canfield, WO 87/00289.

Unfortunately, PNA has its limitations as an anti-TF antigen reagent, as it reacts with other glycoconjugates. Thus, Shysh, et al., Eur. J. Nucl. Med., 10: 68-74 (1985) states that "it has been recognized that PNA is not as specific as human anti- T for T antigen . . . and that PNA binds to some nonmalignant tissues, although to a lesser extent than to the malignant tissues". This sentiment is echoed by Orntoft, et al. (1985), supra, who declares that "it seems that PNA does not bind to immunoreactive T antigen exclusively". Wolf, et al., Cancer Res., 46: 1779-82 (1986), suggests that the "specificity of PNA is directed to the $\alpha$- and $\beta$-configuration of Gal (1→3) GalNAc as well as to galactose alone".

Yuan, et al., Cancer Res., 46:4841-47 (1985) found that while PNA had a sensitivity of the $\beta$-D Gal (1→3 GalNAc structure in cancer tissues of 91%, it showed a specificity of 68% with autopsy controls and 86% with nonneoplastic disease mucosa. Yuan pointed out that PNA also binds $\beta$-D-Gal residues at the nonreducing end of glycoconjugate carbohydrate side chains.

Monoclonal Antibodies As Diagnostic Reagents for Detecting the TF Epitope

Anti-TF MAbs prepared using neuraminidase treated human red blood cells as the immunogen have been previously reported by Rahman et al. in *J. Immunol*, 129: 2021-2024, 1982 and Longenecker et al., *Int. J. Cancer*, 33: 123-129, 1984. One of these monoclonal antibodies, MAb 49H.8, was found to be reactive against a variety of human and murine tumors. Several recent studies have demonstrated the usefulness of MAb 49H.8 as a tool for studying the tumor specificity for MAb 49H.8 as an anti-TF reagent as compared to peanut agglutinin and polyclonal antibodies, [19,20].

Wolf, et al. (1986), supra, reported that MAb 49H8 bound only to certain carcinoma cell lines. Specifically, it bound to BT-20 (breast), MCF-7 (breast), CAMA (breast), TCCSUP (bladder) and SK-LC-4 (lung), but not to SW-1222 (colon), SW-837 (colon), T-24 (bladder) or 2774 (ovary). All of these cell lines were, however, marked by PNA.

Yuan et al., Cancer Res., 46:4841-47 (1985) reported that an anti-TF monoclonal antibody (obtained using neuraminidase- treated human RBCs as the immunogen and commercially available from Chembiomed, Ltd., Edmonton, Alberta, Canada) had 100% specificity for cancer tissue, but a sensitivity of only 76%.

Other anti-TF monoclonal antibodies are known. Longenecker, et al., JNCI, 78: 489-492 (1987); Clausen, et al., Molec. Immunol., 25: 199-204 (1988).

Sandwich Immunoassays

David et al., in U.S. Pat. No. 4,376,110, disclose sandwich immunometric assay techniques for determination of the presence and/or concentration of antigenic substances in fluids using monoclonal antibodies. One monoclonal antibody is presented in a soluble labelled form, and a second monoclonal antibody is bound to a solid carrier. David teaches that it is important that the monoclonal antibody have a high affinity for the antigen, preferably at least $10^8$ liters/mole, and more preferably, at least $10^9$ liters/mole. David does not recognize that lectins may replace antibodies in a sandwich assay, and indeed teaches against such a substitution in view of the relatively low affinity of lectins for their targets

Lectin-Antibody Sandwich Assays

Kinoshita, et al., Clin. Chim. Acta., 179:143-152 (1989) describes an assay for the glycoprotein alpha-fetoprotein in serum comprising incubating a serum sample first with an insolubilized anti-AFP polyclonal antibody and then with a peroxidase-labeled lectin. The lectins used were erythragglutinating phytohemagglutinin, wheat germ agglutinin, concanavalin A, and *Lens culinalis* agglutinin. None of these recognizes Gal($\beta 1 \rightarrow 3$) GalNAc or even the component Gal or GalNAc monosaccharide. However, the article broadly suggested that the method could be applied to characterization of glycoproteins in general.

Kottgen, et al., Biol. Chem. Hoppe-Seyler, 369:1157-1166 (October 1988) discloses an assay for glycosylated fibrinogen employing a deglycosylated solid phase anti-fibrinogen polyclonal antibody and a peroxidase-labelled lectin. The analyte was first incubated with the solid phase antibody. A wash step removed unbound accompanying glycoproteins which could compete later for lectin binding. The lectins employed included PNA.

Canfield, WO87/00289, published Jan. 15, 1987 teaches a method of detecting soluble desialylated glycoproteins in biological fluids. His assay preferably uses a solid phase lectin and a labeled antibody, but he recognizes that the roles of the lectin and the antibody may be reversed. The desialylated glycoproteins of interest to Canfield were desialylated hCG, thyroglobulin, CEA and CA19-9.

For use of covalent lectin-antibody conjugates in immunoassays, see Chu, U.S. Pat. No. 4,371,515 (1983); Chu, U.S. Pat. No. 4,259,747; Guesdon and Avrameas, J. Immunol. Meth., 39:1-13 (1980).

None of these assays related to detection of antigens bearing the TF-disaccharide or the Tn disaccharide. PNA's reactivity with normal tissue would have discouraged use of a lectin-antibody assay for TF antigen rather than a dual antibody immunoassay as taught by David.

No admission is made that any of the foregoing references are available as prior art, or are pertinent prior art. The descriptions are based solely on the publications and no admission is made that the work described in the articles was in fact performed, or that the publication date given is correct or exact. All references cited herein are incorporated by reference to the extent pertinent.

SUMMARY OF THE INVENTION

It is an object of the present invention to overcome the aforementioned deficiencies in the prior art.

One object of the present invention to provide an assay for detection and quantitation of TF antigen in body fluids. Such an assay may be used for early diagnosis of cancer, to prognosticate the clinical course of the cancer, or to monitor response to therapy.

It may also be used to provide a quality control test for various TF antigen preparations.

A murine monoclonal antibody (MAb 49H.8) developed against neuraminidase treated human red blood cells was reactive against a variety of human tumors. The human tumor associated TF antigen detected by this antibody has now been characterized from a human transitional bladder carcinoma cell line (647V), a human colon adenocarcinoma cell line (LS174T), and a pleural effusion fluid of a breast adenocarcinoma patient (PE 89).

A heterologous sandwich radioimmunoassay for TF antigen was developed using MAb 49H.8 as the catcher and $^{125}$I-peanut agglutinin as the probe.

Studies on TF antigen in serum samples using this assay showed that the majority of the carcinoma samples contained higher levels of the antigen as compared to a group of normal samples. These studies demonstrated that the TF antigen is shed by the tumor cells both in vitro and in vivo.

The TF antigen was sensitive to treatment with alkali (0.1 M NaOH for five hours at 37° C.) and periodate (10 mM sodium periodate for one hour at room temperature), was resistant to acidic pH (50 mM acetate buffer, pH 4.5 for five hours at 37° C.), and could be extracted with perchloric acid (0.6 M for one hour at 4° C.). The antigen was shown to be a high molecular weight protein ($M_r > 1,000,000$) by gel filtration chromatography. The density of the antigen was estimated to be 1.35 g/ml by cesium chloride density gradient centrifugation Immunoprecipitation of TF antigen using MAb 49H.8 from a detergent extract of 647V cells with cell surface glycoconjugates labelled with $^3$H showed it to be a glycoprotein with approximate $M_r$ 1,000,000. The human TF antigen of the present invention which is expressed by carcinoma cells and secreted into the body fluids is a mucin-like high molecular weight glycoprotein. The purified antigen is useful as a diagnostic and therapeutic agent.

Thus another object of the present invention to provide a human tumor associated TF antigen, especially in a purified form. This antigen may be used for specific immunotherapy of cancer patients as a reference in sandwich assays for TF antigen in body fluids, and as an immunogen for the generation of new monoclonal antibodies against TF antigen. Also in labeled form, it may be used as an antigenic reagent in a competition immunoassay for detection of TF antigen in body fluids.

A third object is to assay Tn antigen, preferably by an assay analogous to that set forth herein for TF antigen, and to use the Tn/TF ratio to predict the course of the cancer.

BRIEF DESCRIPTION OF THE DRAWINGS

FIGS. 3a and 3b show gel filtration of chromatography of the human TF antigen using 647V conditioned medium (3a) or PE 89 (3b).

DETAILED DESCRIPTION OF THE INVENTION

Figure 1:
FIG. 1 shows the immunoperoxidase staining of 647V cells with MAb 49H.8.

In one aspect, the present invention relates to sandwich immunoassays for antigens in which an immobilized monoclonal antibody is used as the "catcher" and a labeled lectin is used as the "probe". The antibody and the lectin must be capable of binding simultaneously to the antigen to form a ternary complex detectable by virtue of the label. Such a complex may be formed if the antibody and the lectin recognize binding sites which are spatially separated so as to avoid steric hindrance; the binding sites may be the same or different. While the lectin necessarily binds to a carbohydrate target site, this need not be the case for the antibody. The assay may be qualitative or quantitative.

In a preparative step of the assay, the sample may be purified, and/or may be treated chemically or enzymatically to expose a cryptic epitope on the antigen of interest, e.g., with neuraminidase to remove sialic acid masking on, e.g., a carbohydrate epitope. The sandwich immunoassay may be conducted in a forward format (sample is first incubated with the insolubilized antibody), a reverse format (the sample is first incubated with the labeled lectin), or a simultaneous format (the sample is contacted with the insolubilized antibody and the labeled lectin at the same time). The lectin may be any lectin having the desired carbohydrate affinity and specificity. The preferred lectin is PNA. However, other lectins which specifically bind the TF-epitope, such as the jackfruit (*Artocarpus ontegrifolia*) lectin, see Sastry, J. Biol. Chem., 261: 11726-33 (1986), hereby incorporated by reference, may be employed.

PNA has an affinity for the TF disaccharide of about $10^{-6}$. Its affinity for our human tumor-associated TF antigen is much higher, on the order of $10^{-9}$.

The monoclonal antibody may be prepared according to conventional techniques using a natural or synthetic immunogen which is immunologically cross-reactive with the antigen to be detected.

The preferred anti-TF monoclonal antibody is the commercially available (Chembiomed. Ltd., Edmonton, Alberta, Canada) antibody 49H.8. Methods for preparation of MAb 49H.8, and its reactivity with tumor tissues and cell lines, have been disclosed by Longenecker et al., *Int. J. Cancer*, 33: 123-129, 1984, which article is hereby incorporated by reference. The TF disaccharide causes 33% inhibition in binding of 49H.8 to neuraminidase-treated erythrolytes at an inhibitor concentration of 2 mg/ml. The beta anomer caused 29% inhibition, and D-Gal alone only 5%.

Moreover, other monoclonal antibodies of similar immunological characteristics, such as 49H.24 (Id.) and MAb 155H.7 (Longenecker, et al., 1987) may be substituted for MAb 49H.8. The antibody is preferably an IgM antibody.

The labeled lectin may be provided directly or indirectly with any label customarily used in immunoassays or lectin binding assays, including radiolabels, fluorescent labels and enzymatic labels. The labeling process must not, of course, alter overmuch the carbohydrate affinity or specificity of the lectin. A radioisotope is a preferred label.

The "catcher" antibody may be insolubilized directly or indirectly on any conventional support, such as a filter paper, microtiter plate, test tube, dipstick or bead, using any technique that does not substantially detract from the desired immunological activity. The support may be made of any suitable material.

The specificity of the lectin or antibody for the Gal$\beta$(1→3) GalNAc epitope need not be absolute, provide that the cross-reactivity with other epitopes is not so great as to introduce a clinically unacceptable level of false positives.

The present assay is particularly sensitive because a positive reactivity in this assay depends on the ability of the antigen to meet the epitope requirements of two different anti-TF reagents, (e.g., MAb 49H.8) and a lectin (e.g., PNA). This substantially reduces the possibility of a false positive signal due to the non-specific reactivity of either of the reagents. This is evident in the low background signal in the TF antigen assay of this invention, as shown in Table 1.

The assay of the present invention is suitable for detection or quantitation of TF antigens, and especially tumor-associated TF antigens, from a variety of sources, such as cell extracts, conditioned culture medium (secreted TF antigens), pleural effusions, serum samples, and synthetic TF antigens.

The assay, as described thus far, utilizes an insolubilized antibody and a labeled lectin. However, the insolubilized and labeled binding molecules may be interchanged so that the lectin is insolubilized and the antibody is labeled. Preferably, the species which is more specific for the antigen is insolubilized, and preferably, the assay is conducted in a forward format so that this more specific reagent can "purify" the antigen from the sample. MAb 49H.8 is more specific than PNA.

In another embodiment, the assay is adapted for the detection or quantitation of the Tn antigen. The immunodeterminant group of the Tn antigen is GalNAc alpha linked to the hydroxyl group of serine or threonine. The Tn antigen is related to the TF antigen; the enzyme $\beta$-galactosyltransferase adds Gal in a $\beta$-1→3 linkage to the GalNAc of the Tn antigen, thus forming the TF epitope.

In an assay for the Tn antigen, the preferred "catcher" is the antibody MAb 49H.8; the preferred "probe" is *Dolichos Biflorus* Agglutinin. DBA has an affinity constant for the Tn hapten of $4.2 \times 10^3$ liters/mole at 3° C. As in the case of the TF assay, other antibodies and lectins of comparable or superior affinity and specificity for Tn may be substitute for those named, and the roles of "catcher" and "probe" may be reversed.

In a preferred embodiment, a sample of a biological fluid is divided into two portions. One portion is assayed for TF and the other for Tn. The ratio of Tn to TF is calculated. It is believed that the higher this ratio, the worse the prognosis for carcinoma patients.

Summers, et al., Cancer Res., 43:934-39 (1983) teaches that the combination of expression of the normally cryptic TF antigen with higher diploidy is indicative of high risk bladder carcinomas. Springer, et al., Science, 224:1198-1206 (1984) reported that there was a correlation between density of TF and Tn receptors on tumor cell surfaces and tumor invasiveness. Two highly invasive murin human lines had more Tn than TF on their outer cell surfaces.

In a second aspect, this invention relates to human tumor-associated TF antigens, their isolation, and their use in diagnosis and therapy. Human tumor associated TF antigens have been isolated in cell-free form from three different sources: 1) 647V cells; 2) LS174T cells, and 3) pleural effusions of a breast carcinoma patient (PE 89). The molecular characteristics of the TF molecules isolated from each of these sources are similar.

The features of the TF molecules of the present invention, which singly or in combination are indicative of its novelty, are summarized as follows:

1. The TF antigen is a protein of high molecular weight (Mr > 1,000,000).
2. The TF antigen is a glycoprotein with multiple TF epitopes.
3. The human TF antigen is reactive with both PNA and MAb 49H.8 without neuraminidase treatment, and can be detected and quantitated by a sandwich immunoassay as detailed below.
4. The epitope detected by MAb 49H.8 and/or PNA is sensitive to alkali (0.1N NaOH) treatment and periodate treatment (10 mM sodium periodate) but is resistant to acid (50 mM sodium acetate, pH 4.5) treatment.
5. The human TF antigen is extractable by 0.6 M perchloric acid.
6. The human TF antigen is associated with about 90% of human carcinomas, and is not present in the corresponding normal tissues.
7. The human TF antigen is secreted by the carcinoma cells both in vitro and in vivo.

The following table contrasts our human tumor-associated TF antigen with other TF epitope-bearing molecules that have been studied:

of labelled antibody measured for a control sample prepared in accordance with the above, the control samples having a known quantity of TF antigen.

The assay of the present invention is particularly applicable for detection and quantitation of TF antigen in various body fluids, such as serum, pleural effusions, and urine, of carcinoma patients. This is particularly important clinically because the assay provides early detection of cancer, as increased TF antigen expression is associated with certain premalignant changes of tissues (14,15). Similarly, it is possible to detect increased levels of TF antigens in carcinoma patients before cancer tissues reaches a critical mass which is detectable by other non-invasive methods. In these cases the assay is particularly valuable for its early diagnosis of cancer.

Since the human TF antigen can also be used as a prognostic marker in bladder carcinomas (10-13), the assay of the present invention is useful as a prognostic test.

Therapy can easily be monitored using the test of the present invention. Correlation of TF antigen expression with tumor burden and tumor progression gives the capability of monitoring the response of the tumor to anti-cancer treatment.

More generally, the assay of the present invention is useful as a quality control test for various TF antigen preparations. The assay is suitable for ascertaining the immunological reactivity of a variety of TF antigen preparations, both natural and synthetic, and is quantitative.

The human tumor associated TF antigen of the present invention can be used as an agent in active specific immunotherapy of cancer patients. A murine TF antigen, epiglycanin, as well as various synthetic TF antigens, have been previously shown to be effective in eliciting effective anti-cancer immunity in animal models.

Comparisons of human tumor associated TF antigen with other molecules having TF or cryptic TF epitopes.

| Characteristics | Human Tumor-Associated TF Antigen | Epiglycanin[a] | Glycoprotein[b] | LS174T[c] Mucin |
|---|---|---|---|---|
| 1. Origin | 1. Human tumor cell lines 2. Human plural effusion from carcinoma patients | Murine mammary carcinoma cell line | Human red blood cells | Human tumor cells line |
| 2. Molecular weight | >1,000,000 | 500,000 | 31,000 | >1,000,000 |
| 3. TF epitope | non-cryptic | non-cryptic | cryptic | cryptic |
| 4. Reactivity Mab 49H.8 | Reactive | Reactive | Not Reactive | Not Reactive |
| 5. Density (g/mL) | 1.35 | >1.4[d] | — | 1.35-1.5 |

[a]1. Codington J. F. et al. Carbohydr. Res. 40: 171-182, 1975
2. Van den Eijnden D. H., et al. J. Biol. Chem. 254: 12153-12159, 19
[b]1. Marchesi V. T. et al. Ann. Rev. Biochem. 45: 667-698, 1976
2. Prohaska R., et al. J. Biol. Chem. 256: 5781-5791, 1981
[c]Byrd, J. C., et al. Cancer Res. 48: 6678-85, 1988
[d]based on our studies.

In a preferred embodiment, the TF antigen is determined in a fluid by contacting a sample of the fluid with a measured amount of insolubilized antibody to form an insoluble complex of the monoclonal antibody and the TF antigen present in the sample. After a suitable incubation, e.g., about 2 hours, the bound TF antigen is separated from the remainder of the sample (e.g. by washing). The insoluble complex is next contacted with a labeled peanut agglutinin in order to form an insoluble ternary complex of the labeled peanut agglutinin, the TF antigen, and the monoclonal antibody bound to the solid carrier. The solid carrier is then separated from the unreacted labelled PNA. The amount of labelled PNA associated with the solid carrier, or the amount of unreacted labelled PNA is measured, and the amount of labelled antibody measured is related with the amount Human TF antigen may be used as an immunogen for the generation of new monoclonal antibodies against TF antigen, or as a reference in assaying samples containing an unknown quantity of the antigen.

Labelled TF antigen may be used in a competition immunoassay for detection of TF antigen in body fluids. In such an assay, a receptor for the TF disaccharide is provided. This receptor may be an anti-TF monoclonal antibody, such as 49H.8, or an anti-TF lectin, such as PNA. A known quantity of a labeled human tumor associated TF antigen is allowed to compete with the TF antigen of the sample for the TF disaccharide binding sites of the receptor. The receptor may be insolubilized before or after the competition step, and bound labeled TF antigen separated from unbound labeled antigen. Or the label may be of such character that a different signal is produced if the labeled antigen is bound to the receptor, than if it is not so bound. The incubation of the sample with the receptor may precede, follow or coincide with the incubation of the labeled antigen with the receptor.

EXAMPLE 1

Detection of Human Tumor-Associated TF Antigen

Cell Line, Culture, Conditioned Medium, and Extraction

The cells cultured were a human bladder transitional cell carcinoma cell line, a human adenocarcinoma cell line, LS174T (obtained from the American Type Culture Collection, Rockville, Md.), and a murine mammary adenocarcinoma cell line (Ta3-Ha). The cells were cultured in RPMI 1640 medium supplemented with FBS (5%) and gentamicin (50 units/mL), and the medium was changed every three days. The spent conditioned medium was collected during each medium change, pooled together, centrifuged at 10,000×g for 30 minutes to remove the cell debris, and concentrated about 20 fold using a High-Output Stirred Cell 2000 (Amicon Corporation, Danvers, Mass.). When confluent, the cells were removed from the flasks by 0.02% EDTA treatment followed by scraping with a rubber policeman. The cell suspension, approximately 10a cells, was washed in PBS (phosphate buffered saline) three times, and the pellet was extracted with a detergent (NP-40 or octyl glucoside) extraction buffer (1% NP-40 or 1% octyl glucoside, 2 mM EDTA, 1 mM phenylmethylsulfonyl fluoride, 2 mM pepstatin, 10 mM o-phenanthroline, and 150 mM NaCl in 50 mM Tris buffer, pH 7.5) for 30 minutes at 4° C. and centrifuged at 30,000×g.

Monoclonal Antibodies, PNA, and Iodination

MAb 49H.8 (isotype: IgM) was prepared and purified as reported by Rahman et al., *J. Immunol.* 129: 2021-2024, 1982; and Longenecker et al., *Int. J. Cancer*, 33: 123-129, 1984, which articles are hereby incorporated by reference. PNA was obtained from E-Y Laboratories, San Mateo, Calif. MAb CH4 (30 and MOPC-104E (sigma Chemical Co.) were used as negative control antibodies. PNA was radioiodinated by the Iodo-Gen method.[31]

Immunoperoxidase Staining

Immunoperoxidase staining of cells was conducted according to the avidin-biotin peroxidase complex (ABC) method of Hsu et al., *J. Histochem. Cytochem.*, 29:577-580, 1981, which article is hereby incorporated by reference. The cells were grown on glass cover slips, then air dried, and sequentially incubated with a primary antibody, MAb 49H.8, at room temperature for 15 minutes, with 0.025% glutaraldehyde at 4° C. for five minutes, with biotinylated anti-mouse IgM at room temperature for 30 minutes, and with ABC reagent at room temperature for 20 minutes. After each of the above steps, the slides were washed in phosphate buffered saline at room temperature for five minutes. The slides were then incubated with 3,3'-diamino benzidine substrate solution containing 0.5% hydrogen peroxide at room temperature for five minutes, washed in water, counterstained with hematoxylin, and mounted in permount. A brown color corresponds to positive reaction with the antibody.

The reactivity of MAb 49H.8 with 647V cells was demonstrated by immunoperoxidase staining of these cells with MAb 49H.8, as shown in FIG. 1. Similarly, the reactivity of LS174T cells with MAb 49H.8 was also demonstrated by immunoperoxidase staining.

Sandwich Radioimmunoassay of Cell Extracts, Conditioned Media and Pleural Effusions Nonionic detergent (NP-40 or octyl glucoside) extracts of 647V and LS174T cells, culture media conditioned by these cells, and a pleural effusion from a breast cancer patient (PE 89) were tested for TF antigen using a heterologous sandwich radioimmunoassay. Epiglycanin, a murine TF antigen, and TF($\alpha$)-HSA, a synthetic TF antigen, served as positive control samples, while HSA, fresh culture media, and detergent extraction buffers served as negative control samples. An isotype matched (IgM) myeloma protein (MOPC-104E) was used further to confirm the specificity of this assay.

Breakable strips of microtitre wells were coated with MAb 49H.8 or a control antibody (MOPC-104E), 1 µg/well, by overnight incubation at 4° C. The wells were then serially incubated with FBS 5% in PBS at 37° C. for 30 minutes, with antigen solution at 37° C. for two hours, and with radioiodinated PNA ($2\times10^5$cpm/well) at room temperature for two hours. The wells were washed with PBS containing 0.05% Tween-20 after each of the above steps. Each well was counted for $^{125}$I activity using a gamma counter.

The results are summarized in Table 1. MOPC-104E did not show any selective reactivity with any of the samples used in this assay, demonstrating the specificity of the positive reactivity with MAb 49H.8. While MAb 49H.8 showed positive reactivity with epiglycanin and TF(o)-HSA, no significant reactivity was observed for negative control samples, demonstrating the selectivity of the assay for TF antigen. The detergent extracts of 647V and LS174T cells, conditioned culture media from these cells, and PE 89 showed strong positive reactivity for TF antigen. The inhibition of the antigen capture by synthetic carbohydrate haptens was effected to demonstrate further the specificity of the assay, as shown in Table 2. The positive reactivity in this assay could be inhibited by phenyl-$\beta$-D-galactoside and p-nitrophenyl-$\beta$-D-galactoside in a concentration dependent manner as expected, while non-specific haptens such as phenyl-$\beta$-D-glucoside and p-nitrophenyl-$\alpha$-D-galactoside did not show any inhibition.

Sandwich RIA of Serum Samples

Serum samples of normal and carcinoma patients were diluted with equal volume of PBS and assayed for TF antigen using the sandwich radioimmunoassay described above.

Figure 2:
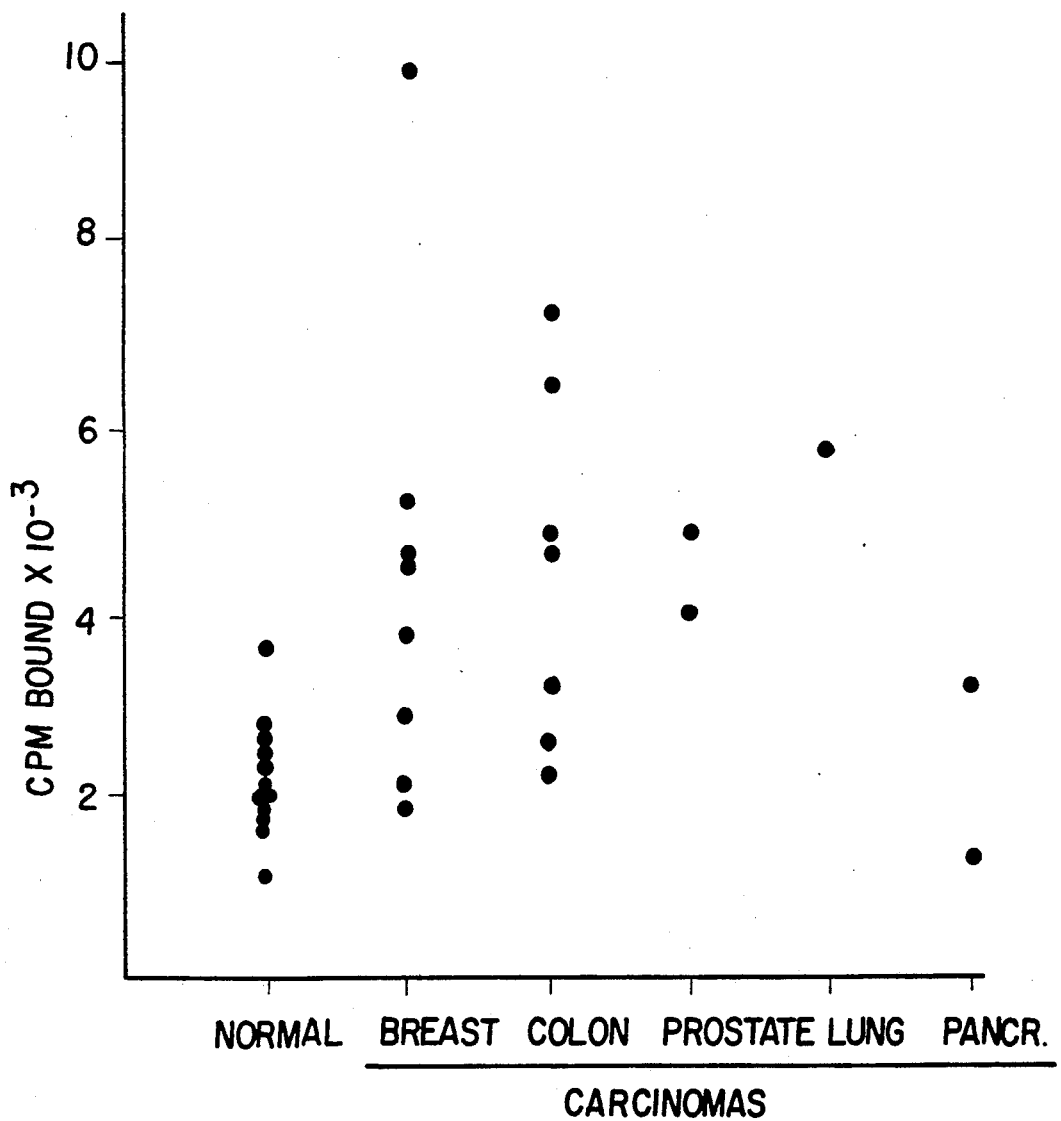
FIG. 2 shows TF antigen analysis of human serum samples using SRIA

The results are summarized in FIG. 2. The TF antigen levels are expressed in terms of cpm of $^{125}$I-PNA bound. The majority of the carcinoma serum samples showed higher levels of TF antigen as compared to a group of normal serum samples.

EXAMPLE 2

Characterization of Human Tumor-Associated TF Antigen

Chemical Treatment of Antigen

Antigen solutions were incubated with 0.1 M NaOH 50 mM acetate buffer (pH 4.5) or PBS at 36° C. for five hours, neutralized to pH 7.5, then dialysed against PBS overnight at 4° C.

Periodate treatment of the antigen solutions was done based on a procedure reported by Woodward et al., *J. Immunol. Methods* 78:143-153. 1985, which article is hereby incorporated by reference. Antigen solutions were incubated with 10 mM sodium periodate in 50 mM acetate buffer (pH 4.5) at room temperature in the dark for one hour, neutralized to pH 7.5, incubated with 1% glycine for 15 minutes at room temperature, and then dialyzed against PBS overnight at 4° C.

Antigen solutions were incubated with 0.6 M perchloric acid at 4° C. for one hour, followed by removal of the precipitate by centrifugation at 10,000×g for fifteen minutes. The supernatants were dialyzed against PBS overnight at 4° C. The TF activity of all of the above samples was evaluated by sandwich radioimmunoassay as described above.

The effect of various chemical treatments on the TF activity of 647V conditioned medium, LS174T conditioned medium, and PE 89 and Ta3-Ha conditioned medium (positive control sample) are shown in Table 3. Incubation with 0.1 M NaOH at 37° C. for five hours completely abolished the reactivity of all of the samples, whereas incubation with PBS or 50 mM acetate buffer (ph 4.5) at 37° C. for five hours resulted in little or no loss of activity. A periodate treatment of the antigen samples was carried out under conditions reported to be suitable for the selective destruction of carbohydrate moieties without significant alteration of the protein epitopes. Periodate treatment resulted in 100% loss of reactivity for all of the samples. The recovery of TF activity after perchloric acid extraction for 647V conditioned medium, Ta3- Ha conditioned medium, and PE 89 were 100%, and that for LS 176T conditioned medium was 86%.

Gel filtration Chromatography

Tumor cell (G47V and LS174T) detergent extracts, concentrated conditioned media from cell culture, or pleural effusion fluid (PE 89) were fractionated on a Superose HR-12 gel filtration column using a fast protein liquid chromatography (FPLC) system. The elution was conducted under isocratic conditions using 0.2 M phosphate buffer (pH 7.5) containing 0.15 M NaCl or 6 M guanidine hydrochloride in 0.1 M phosphate buffer (pH 7.5) containing 0.15 M NaCl or 6 M guanidine hydrochloride in 0.1 M phosphate buffer (pH 7.5) with 0.15 M NaCl at a flow rate of 0.3 mL per minute. The eluant fractions (0.6 mL each) were assayed for TF antigen by sandwich radioimmunoassay either directly or after overnight dialysis (in the case of elution by 6 M guanidine hydrochloride buffer) against PBS.

Figure 3B:
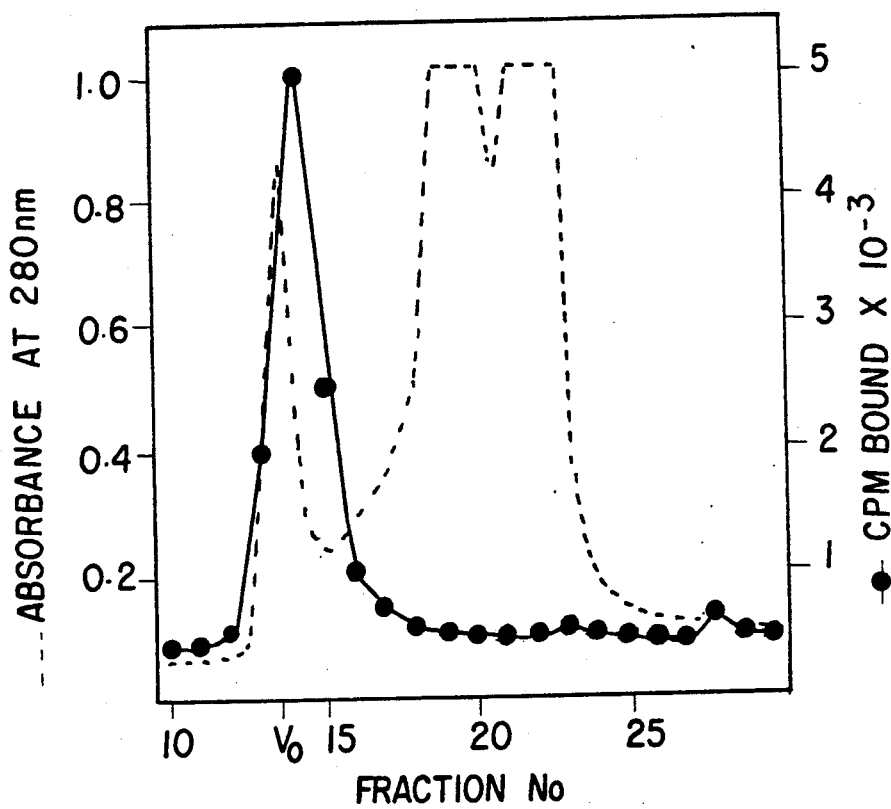

Typical chromatograms of 647V cell conditioned medium, and PE 89, are shown in FIGS. 3a and 3b. The chromatograms 647V cell extract, of LS174T cell extract, and LS174T conditioned medium were similar to those shown in FIG. 3a. In all of the above chromatograms, MAb 49H.8 reactivity was limited to the void volume fractions as shown by the sandwich radioimmunoassay, suggesting that the molecular weight of the TF antigen is greater than $10^6$. The void volume fractions having TF activity from 647V conditioned medium or PE 89 were pooled together and subjected to reduction of any disulfide bonds by treatment with dithiothreitol, the thiol groups were alkylated by treatment with iodoacetamide, and subjected to gel filtration chromatography using 6 M guanidine hydrochloride buffer as the eluant. The eluants were assayed for TF activity by sandwich radioimmunoassay. The gel filtration chromatograms were similar to those shown in FIGS. 3a and 3b, and the TF activity was associated exclusively with the void volume fractions.

Reduction and Alkylation

A high molecular weight fraction enriched in TF antigen from 647V cell conditioned medium or PE 89 was subjected to reduction by incubation with 50 mM dithiothreitol in the presence of 6 M guanidine hydrochloride at 4° C. for 18 hours, alkylated by incubation with 150 mM iodoacetamide in the dark at room temperature for one hour, and the excess iodoacetamide was destroyed by the addition of 200 mM dithiothreitol. This solution was further fractionated by gel filtration chromatography using guanidine hydrochloride buffer, and the fractions were assayed by sandwich radioimmunoassay as described above.

Affinity Chromatography

An affinity column was prepared by conjugation of MAb 49H.8 with CNBr activated Sepharose 4B beads according to the procedure supplied by the supplier, Pharmacia. The antigen solution (647V conditioned medium) was incubated with the affinity beads at room temperature overnight, and then washed with PBS. The column was then eluted with 50 mM glycine buffer containing 150 mM NaCl (pH 2.8) at a flow rate of 0.5 ml/min. the fractions (0.5 ml each) were collected and analyzed for TF antigen by sandwich radioimmunoassay.

Figure 4:
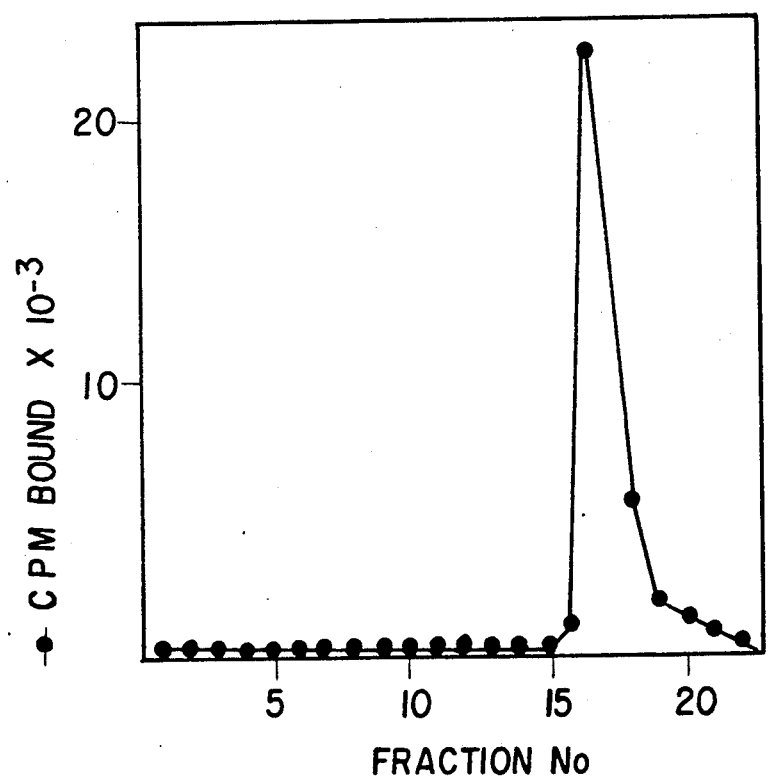
FIG. 4 shows affinity chromatography of 647V conditioned medium, showing TF activity of each fraction.

FIG. 4 shows that the fractions of the conditioned medium passed through the column, and that the PBS washings were free of any TF activity. The TF activity was limited to the fractions eluted with acidic pH.

Cesium Chloride Density Gradient Centrifugation

The density of the antigen solution was adjusted to 1.45 g/mL using cesium chloride. Five mL of the solution was centrifuged at 150,000×g for 72 hours in a Beckman ultracentrifuge using a SW 50.1 rotor at 4° C. Fractions of 0.2 mL each were collected, the density was determined gravimetrically, the fractions were dialyzed against PBS overnight at 4° C., and then assayed for TF antigen by sandwich radioimmunoassay.

Figure 5:
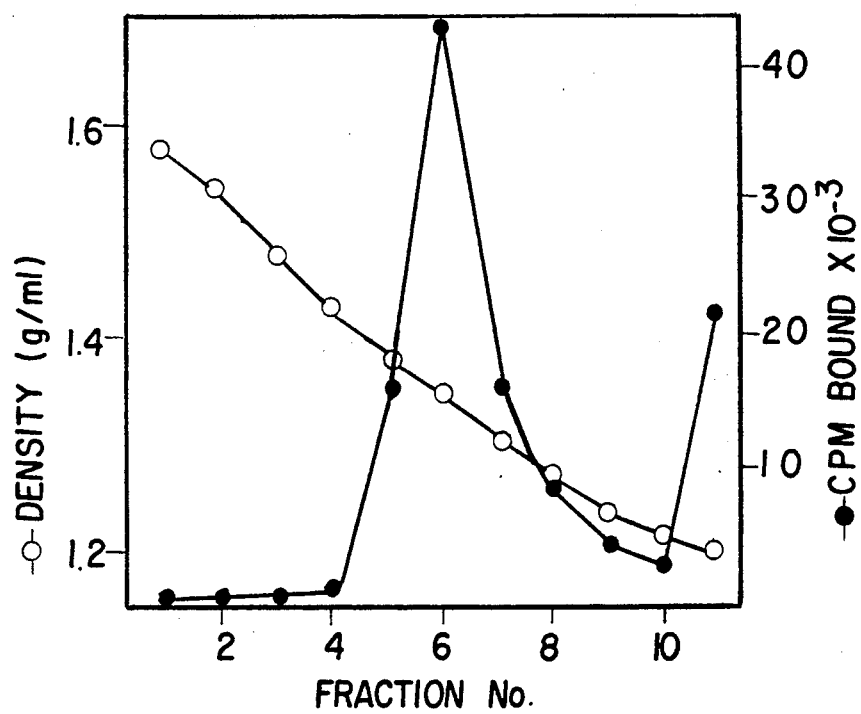
FIG. 5 shows the cesium chloride density gradient ultracentrifugation of 647V centrifuged medium.

Analytical cesium chloride density gradient centrifugation of 647V conditioned medium, as shown in FIG. 5, showed that the major peak with TF activity was associated with a density of approximately 1.35 g/mL. An additional peak with a density of 1.3 g/mL was also noted.

Tritium Labelling of Cell Surface Glycoconjugates

The carbohydrate residues on the cell surface of 647V cells were labelled with tritium and a detergent (NP-40) extract of these radio-labelled cells was used for immunoprecipitation of the TF antigen. Tritium labelling of cell surface glycoconjugates was effected using the galactose oxidase-borohydride method of Gahmberg, Methods Enzymol. 50: 204-206, 1978, which article is hereby incorporated by reference. A single cell suspension of 647V cells ($5 \times 10^7$) in 0.5 mL PBS was gently shaken with five units of galactose oxidase at 37° C. for 30 minutes. The cells were then washed three times in PBS and the pellet was extracted with NP-40 extraction buffer.

Immunoprecipitation of the TF Antigen

An aliquot of the above NP-40 extract was precleared by overnight incubation with anti-mouse IgM-agarose beads at 4 C. The supernatant was divided into three equal portions and incubated with MAb 49H.8, MAb CH4, or normal mouse serum at 4° C. for four hours. Then each of the aliquots was incubated with anti-mouse IgM-agarose beads at 4° C. with gentle shaking overnight. The beads were collected by centrifugation, washed five times with 0.05 M Tris HCl buffer (pH 7.5) containing 0.5 M NaCl, and extracted by boiling with Laemmeli sample buffer. The samples were analyzed by electrophoresis (SDS-PAGE: 3% stacking gel and 3-15% resolving gel) followed by autoradiographic detection of the tritium labelled glycoprotein bands.

Figure 6:
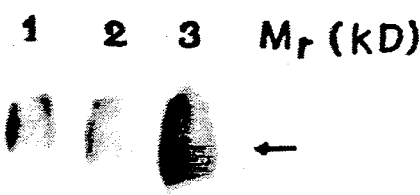
FIG. 6 shows immunoprecipitation of tritium labelled 647V cell extract.

FIG. 6 shows that MAb 49H.8 immunoprecipitated a high molecular weight bank (800,000–1,000,000D), while the control MAb and mouse serum failed to immunoprecipitate any protein selectively.

Summation

The gel filtration chromatography and the immunoprecipitation of the TF antigen show that it is a high molecular weight glycoprotein. The estimation of the exact molecular weight is difficult, since the antigen eluted in the void volume in the gel filtration chromatography, and appeared as a band at the top of the resolving gel in the immunoprecipitation experiment. However, these results suggest that the molecular weight is in the range of $10^6$ D.

The density of the antigen was estimated to be 1.35. The density of proteins is usually less than 1.3, whereas that of proteoglycans is greater than 1.6. The periodate oxidation experiment suggested that the epitope detected by MAb 49H.8 is a carbohydrate. The loss of antigenic activity on incubation with 0.1 M NaOH suggested that the carbohydrate epitopes are 0-linked to the protein core, typical of mucin glycoproteins.

The high molecular weight, presence of multiple O-linked carbohydrate epitopes, and the observed density suggests that the human TF antigen is a mucin. The extractability of the antigen by 0.6 M perchloric acid is consistent with its being a mucin. Byrd et al., in Cancer Res. 48: 6678–6685, 1988, have recently reported the characterization of a cancer associated mucin from LS174T cells. The TF epitope appears to be cryptic in this mucin in that the native mucin was unreactive with the anti-TF antibody MAb 49H.8, whereas the asialo mucin was reactive. Therefore, the molecule of the present invention appears to be different from the one reported by Byrd et al.

The successful radiolabelling of the TF antigen by the tritiation of the cell surface glycoproteins and its subsequent immunoprecipitation suggest that the antigen is expressed on the cell surface. The detection of the antigen in culture media conditioned by the cell lines as well as in the pleural effusion of a breast cancer patient suggest that the TF antigen is shed by cancer cells.

Thus, since the TF antigen thus characterized appears to be shed by cancer cells, cancer can be detected in very early stages by detecting the presence of this TF antigen in body fluids such as urine, serum, and the like. Moreover, the progress of chemotherapy or radiotherapy can be monitored by monitoring the quantity of this TF antigen present in the body fluid of a cancer patient. As the tumor is reduced by the therapy, the amount of this TF antigen in the body is reduced.

EXAMPLE 3

Purification of Human Tumor-Associated TF Antigen and use thereof.

Human tumor-associated TF antigen was purified from conditioned culture medium (used to cultivate LS174T or 647V cell lines) by affinity chromatography using a MAb 49H.8 - CnBr activated Sepharose column. This resulted in an enrichment of about 8,930 based on protein assays of the starting material and the purified preparation. The recovery was 67.5%, as determined by sandwich RIA as previously described. Gel filtration resulted in an additional 13-fold purification, with a recovery of 79.5%.

It is believed that a further enhancement in purity may be obtained by combining the instant procedure with lectin affinity chromatography with insolubilized PNA or other suitable lectin.

These purification steps can be practiced in any order or combination.

EXAMPLE 4

Immunogenic Use of the Purified Human Tumor-Associated TF Antigen

In a preferred protocol for active specific immunotherapy, 3–6 days before first immunization, patients will intravenously receive 200 mg/m$^2$ cyclophosphamide. The first immunization is with 100–500 μg purified human TF antigen intradermally. Similar doses are administered every 2 weeks for 6–8 weeks.

However, this protocol may be modified. Smaller or larger doses may be given, or the number of spacing of doses may be changed. Cyclophosphamide may be omitted, or replaced by another agent which selectively inhibits production of $T_S$ cells. The antigen may be given with an adjuvant, such as DETOX (Ribi Immunochemical) or SAF-1 (Syntex). Immunization with the purified human tumor-associated TF antigen may be combined with immunization with a synthetic TF antigen such as Gal ($\beta1\rightarrow3$) GalNAc/KLH.

The foregoing description of the specific embodiments will so fully reveal the general nature of the invention that others can, by applying current knowledge, readily modify and/or adapt for various applications such specific embodiments without departing from the generic concept, and therefore such adaptations and modifications are intended to be comprehended within the meaning and range of equivalents of the disclosed embodiments. It is to be understood that the phraseology or terminology herein is for the purpose of description and not of limitation.

TABLE 1

| | Sandwich Radioimmunoassay for TF Antigen using $^{125}$I-PNA as a Probe | |
|---|---|---|
| Source of Antigen | MAb 49H.8 as Catcher | MOPC-104E as Catcher |
| PBS | 266 ± 19 | 256 ± 10 |
| 647V cell octyl glucoside extract (1:10 dilution) | 12 086 ± 742 | 1 365 ± 136 |
| Octylglucoside buffer | 205 ± 1 | 276 ± 37 |

TABLE 1-continued

Sandwich Radioimmunoassay for TF Antigen using $^{125}I$-PNA as a Probe

| Source of Antigen | MAb 49H.8 as Catcher | MOPC-104E as Catcher |
|---|---|---|
| (1:10 dilution) LS174T cell NP-40 extract | 9 367 ± 57 | 1 251 ± 60 |
| (1:10 dilution) NP-40 buffer (1:10 dilution) | 266 ± 83 | 298 ± 57 |
| 647V conditioned culture medium (8×) | 37 066 ± 2193 | 322 ± 58 |
| LS174T conditioned culture medium (4×) | 26 035 ± 613 | 206 ± 38 |
| Culture medium (4×) | 540 ± 84 | 153 ± 5 |
| PE 89 (1:2 dilution) | 14 807 ± 1979 | 280 ± 58 |
| TF(α)-HSA (10 μg) | 3 997 ± 199 | 465 ± 32 |
| HSA (10 μg) | 351 ± 51 | 278 ± 25 |
| Epiglycanin (10 μg) | 22 875 ± 80 | 693 ± 197 |

TABLE 2

Inhibition of TF Antigen Binding with MAb 49H.8 by Synthetic Carbohydrates in SRIA

| | | % Inhibition ± SD | | | |
|---|---|---|---|---|---|
| Inhibitor | Concentration mM | 647V Conditioned Medium | LS174T Conditioned Medium | PE89 | Ta3-Ha Conditioned Medium |
| Phenyl-β-D- galactoside | 5 | 66.60 ± 2.58 | 86.95 ± 2.38 | 45.48 ± 5.40 | 69.40 ± 2.15 |
| | 10 | 90.12 ± 5.24 | 95.91 ± 0.30 | 69.04 ± 0.54 | 96.25 ± 0.35 |
| Phenyl-β-D- glucoside | 5 | −3.00 ± 7.99 | −7.15 ± 9.17 | −6.41 ± 7.79 | 3.92 ± 7.35 |
| | 10 | 0.58 ± 4.70 | −1.67 ± 1.87 | −4.61 ± 7.19 | 1.38 ± 0.64 |
| p-nitrophenyl α-D-galactoside | 5 | 72.03 ± 2.97 | 83.39 ± 0.95 | 53.25 ± 1.23 | 58.00 ± 0.14 |
| | 10 | 94.95 ± 1.01 | 95.84 ± 0.13 | 78.69 ± 0.57 | 94.15 ± 0.03 |
| p-nitrophenyl α-D-galactoside | 5 | 14.64 ± 1.82 | 5.75 ± 0.84 | −0.16 ± 6.66 | 2.41 ± 0.78 |
| | 10 | 18.08 ± 1.84 | 10.52 ± 1.82 | 7.51 ± 1.28 | 1.21 ± 2.17 |

TABLE 3

Recovery of TF Activity After Chemical Treatment

| | % Recovery + SD | | | |
|---|---|---|---|---|
| Treatment | 647V Conditioned Medium | LS174T Conditioned Medium | PE89 | Ta3-Ha Conditioned Medium |
| No treatment | 100.00 | 100.00 | 100.00 | 100.00 |
| PBS (37° C. for 5 hours) | 97.09 ± 0.74 | 97.34 ± 1.12 | 95.59 ± 0.89 | 96.21 ± 2.32 |
| 0.1M NaOH (37° C. for 5 hours) | 0.72 ± 0.69 | 13.90 ± 0.65 | 0.00 | 2.33 ± 0.02 |
| 50 mM acetate buffer, pH 4.5 (37° C. for 5 hours | 96.25 ± 4.13 | 98.52 ± 1.46 | 95.36 ± 4 | 93.95 ± 2.24 |
| 10 mM periodate in 50 mM acetate buffer pH 4.5 (RT for 1 hour) | 0.00 | 0.00 | 0.00 | 0.00 |
| 0.6M perchloric acid (4° C. for 1 hour) | 100.57 ± 3.45 | 85.58 ± 1.25 | 104.90 ± 4.25 | 108.43 ± 1.09 |

REFERENCES

1. Springer, G. F. and Desai, P. R. Human blood group MN and precursor specificities. Structural and biological aspects. Carbohdr. Res., 40: 183-192, 1975.

2. Springer, G. F. T and Tn, general carcinoma autoantigens. Science, 224:1198-1206, 1984.

3. Rahman, A. F. R. and Longenecker, B. M. A monoclonal antibody specific for the Thomsen-Friedenreich cryptic T antigen. J. Immunol., 129:2021-2024, 1982.

4. Longenecker, B. M., Rahman, A. F. R., Leigh, J. B.; Purser, R. A., Greenberg, A. H., Willans, D. J., Keller, O., Petrik, P. K., Thay, T. Y., Suresh, M. R. and Noujaim, A. A. Monoclonal antibody against a cryptic carbohydrate antigen of murine and human lymphocytes. I. Antigen expression in non-cryptic or unsubstituted form on certain murine lymphomas, on a spontaneous murine mammary carcinoma, and on several human adenocarcinomas. Int. J. Cancer, 33: 123–129, 1984.

5. Longenecker, B. M., Willans, D. J., MacLean, G. D., Selvaraj, S., Suresh, M. R. and Noujaim, A. A. Monoclonal antibodies to synthetic tumor-associated glycoconjugates in the study of expression of Thomsen-Friedenreich-like and Tn-like antigens on human cancer. J. Natl. Cancer Inst., 78: 489–495, 1987.

6. Henningson, C. M., Selvaraj, S., MacLean, G. D., Suresh, M. R., Noujaim, A. A. and Longenecker, B. M. T-cell recognition of a tumor-associated glycoprotein and its synthetic carbohydrate epitopes: stimulation of anticancer T-cell immunity in vivo. Cancer Immunol. Immunother., 25: 231–241, 1987.

7. Springer, G. F., Murthy, S. M., Desai, P. R. and Scanlon, E. F. Breast cancer patient's cell mediated immune response to Thomsen-Friedenreich antigen. Cancer, 45: 2949–2954, 1980.

8. Springer, G. F., Murthy, S. M., Desai, P. R., Fry, W. A., Tegtmeyer, H. and Scanlon, E. F. Patient's immune response to breast and lung carcinoma associated Thomsen-Friedenreich (T) specificity. Klin. Wochenschr., 60: 121–131, 1982.

9. Wolf, M. F., Ludwig, A., Fritz, P. and Schumacher, K. Increased expression of Thomsen-Friedenreich antigens during tumor progression in breast cancer patients. Tumor Biol., 9: 190–194, 1988.

10. Ohoka, H., Shinomiya, H., Yokoyama, m., Ochi, K., Takeuchi, M. and Utsumi, S. Thomsen-Friedenreich antigen in bladder tumors as detected by specific antibody: a possible marker of recurrence. Urol Res., 13: 47–50, 1985.

11. Summers, J. L., Coon, J. S., Ward, R. M., Falor, W. H., Miller, A. W. III. and Weinstein, R. S. Prognosis in carcinoma of urinary bladder based upon tissue blood group ABH and Thomsen-Friedenreich antigen status and karyotype of the initial tumor. Cancer Res., 43: 934–939, 1983.

12. Coon, J. S., Weinstein, R. S. and Summers, J. L. Blood group precursor T-antigen expression in human urinary bladder carcinoma. Am. J. Clin. Pathol., 77: 692–699, 1982.

13. Limas, C. and Lange, P. T-antigen in normal and neoplastic urothelium. Cancer (Phila.), 58: 1236–1245, 1986.

14. Boland, C. R., Montgomery, C. K. and Kim, Y. S. Alterations in human colonic mucin occurring with cellular differentiation and malignant transformation. Proc. Natl. Acad. Sci. U.S.A., 79: 2051–2055, 1982.

15. Boland, C. R., Montgomery, C. K. and Kim, Y. S. A cancer-associated mucin alteration in benign colonic polyps. Gastroenterology, 82: 664–672, 1982.

16. Itzkowitz, S. H., Yuan, M., Montgomery, C. K., Kjeldsen, T., Takahasi, H. K., Bigbee, W. L., and Kim, Y. S. Expression of Tn, sialosyl-Tn, and T antigens in human colon cancer. Cancer Res., 49: 197–204, 1989.

17. Springer, G. F., Cheingsong-Popov, R., Schirrmacher, V., Desai, P. R. and Tegtmeyer, H. Proposed molecular basis of murine tumor cell-hepatocyte interaction. J. Biol. Chem., 258:5702–5706, 1983.

18. Lotan, R., Skutelskyk, E., Danon, D. and Sharon, N. The purification, composition, and specificity of the anti-T lectin from peanut (Arachis hypogaea). J. Biol. Chem., 250: 8518–8523, 1975.

19. Yuan, M., Itzkowitz, S. H., Boland, C. R., Kim, Y. D., Tomita, J. T., Palekar, A., Bennington, J. L., Trump, B. F. and Kim, Y. S. Comparison of T-antigen expression in normal, premalignant, and malignant human colonic tissue using lectin and antibody immunohistochemistry. Cancer Res., 46: 4841–4847, 1986.

20. Wolf, M. F., Koerner, U. and Schumacher, K. Specificity of reagents directed to the Thomsen-Friedenreich antigen and their capacity to bind to the surface of human carcinoma cell lines. Cancer Res., 46: 1779–1782, 1986.

21. Ravn, V. and Jensen, H. Thomsen-Friedenreich-related antigen in human endometrium. An immunohistochemical study employing the monoclonal antibody 49H.8. A preliminary report. APMIS, 96: 552–558, 1988.

22. Juhl, B. R., Hartzen, S. H. and Hainau, B. Thomsen-Friedenreich-related antigen in non-neoplastic ureter, urothelium and transitional cell tumors of the urinary bladder. An immunohistochemical study employing the monoclonal antibody 49H.8. Acta Pathol, Microbiol. Immunol. Scand. [A], 95: 83–91, 1987.

23. Marchesi, V. T., Furthmayr, H. and Tomita, M. The red cell membrane. Ann. Rev. Biochem., 45: 667–698, 1976.

24. Prohaska, R., Koerner, T. A. W., Armitage, I. M. and Furthmayr, H. Chemical and carbon-13 nuclear magnetic resonance studies of blood group M and N active sialoglycopeptides from human glycophorin A. J. Biol. Chem., 256: 5781–5791, 1981.

25. Codington, J. F., Lonsley, K. B., Leanloz, R. W., Irimura, T. and Osawa, T. Immunochemical and chemical investigations of the structure of glycoprotein fragments obtained from epiglycanin, a glycoprotein at the surface of the TA3-Ha cancer cell. Carbohydr. Res., 40: 171–182, 1975.

26. Van den Eijnden, D. H., Evans, N. A., Codington, J. F., Reinhold, V., Silber, C. and Jeanloz, R. W. Chemical structure of epiglycanin, the major glycoprotein of the TA3-Ha ascites cell. J. Biol. Chem., 254: 12153–12159, 1979.

27. Coon, J. S., Watkins, J. R., Pauli, B. U. and Weinstein, R. S. Flow cyktometric analysis of heterogeneity in blood group-related antigen expression in a human urinary bladder carcinoma cell line, 647V. Cancer Res., 45: 3014–3021, 1985.

28. Tom, B. H., Rutzky, L. P., Jakstys, M. M., Oyawu, R., Kaye, C. I. and Kahan, B. D. Human colonic adenocarcinoma cells. I. Establishment and description of a new cell line. In Vitro, 12: 180–191, 1976.

29. Hsu, S-M., Raine, L. and Fanger, H. Use of avidin biotin-peroxidase complex (ABC) in immunoperoxidase techniques. A comparison between ABC and unlabelled antibody (PAP) procedures. J. Histochem Cytochem., 29: 577–580, 1981.

30. Mosmann, T. R., Gallatin, M., and Longenecker B. M. Alteration of apparent specificity of monoclonal (hybridoma) antibodies recognizing polymorphic histocompatabiity and blood group determinants. J. Immunol., 125: 1152–1156, 1980.

31. Fraker, P. J. and Speck, J. C. Jr. Protein and cell membrane iodinations with a sparingly soluble chloroamide, 1,3,4,6-tetrachloro-3a,6a-diphenyl glycoluril. Biochem. Biophys. Res. Commun., 80: 849–857, 1978.

32. Woodward, M. P., Young, W. W. Jr. and Bloodgood, R. A. Detection of monoclonal antibodies specific for carbohydrate epitopes using periodate oxidation. J. Immunol. Methods, 78: 143–153, 1985.

33. Chase, K. V., Flux, M. and Sachdev, G. P. Comparison of physicochemical properties of purified mucus glycoproteins isolated from respiratory secretions of cystic fibrosis and asthmatic patients. Biochemistry, 24: 7334–7341, 1985.

34. Gahmberg, C. G. Tritium labelling of cell-surface glycoproteins and glycolipids using galactose oxidase. Methods Enzymol., 50: 204–206, 1978.

35. Hascall, V. C. and Kimura, J. H. Proteoglycans: isolation and characterization. Methods Enzymol., 82: 769–800, 1982.

36. Magnani, J. L., Steplewski, Z., Koprowski, H. and Ginsburg, V. Identification of the gastrointestinal- and pancreatic cancer-associated antigen detected by monoclonal antibody 19-9 in the sera of patients as a mucin. Cancer Res., 43: 5489–5492, 1983.

37. Byrd, J. C., Nardelli, J., Sidiqui, B. and Kim, Y. S. Isolation and characterization of colon cancer mucin for xenographs of LS174T cells. Cancer Res., 48: 6678–6685, 1988.

38. Linsley, P. S., Brown, J. P., Magnani, J. L. and Horn, D. Monoclonal antibodies reactive with mucin glycoproteins found in sera from breast cancer patients. Cancer Res., 48: 2138–2148, 1988.

39. Patterson, A. J., Schlom, J., Sears, H. F., Bennet, J. and Colcher, D. Radioimmunoassay for the detection of a human tumor associated glycoprotein (TAG-72) using monoclonal antibody B72.3. Int. J. Cancer, 37: 659–666, 1986.

What is claimed is:

1. A human, tumor-associated glycoprotein antigen characterized by a non-cryptic Gal beta (1→3) GalNAc epitope, a molecular weight in excess of 1,000,000 daltons, and extractability with perchloric acid, the eptitope being sensitive to alkali and periodate but resistant to acid, in at least partially purified form.

2. A reference reagent comprising a known quantity of the antigen of claim 1 in an immunologically acceptable carrier.

3. A reagent comprising the antigen of claim 1 in labeled form.

4. A reagent comprising the antigen of claim 1 in insolubilized form.

5. The antigen of claim 1, said antigen being obtained by affinity chromatography with a MAb 49H8-CnBr activated agarose column.

6. A human, tumor-associated glycoprotein antigen characterized by a non-cryptic Gal beta (1→3) GalNAc epitope, a molecular weight in excess of 1,000,000 daltons, and extractability with perchloric acid, the epitope being sensitive to alkali and periodate but resistant to acid, in at least partially purified form, said antigen being isolated by affinity chromatography of antigenic material derived from adenocarcinoma conditioned media, adenocarcinoma cell detergent extracts or pleural effusion fluid with an insolubilized TF-specific monoclonal antibody having the binding characteristics of MAb 49H.8.

* * * * *